(12) United States Patent
Kulmala et al.

(10) Patent No.: US 9,535,029 B2
(45) Date of Patent: *Jan. 3, 2017

(54) LOW-COST ELECTRODE CHIP VARIANTS AND METHODS FOR MULTI ANALYTE ANALYSIS AND REFERENCING BASED ON CATHODIC ELECTROLUMINESCENCE

(75) Inventors: Sakari Kulmala, Kirkkonummi (FI); Antti Niskanen, Espoo (FI); Aija Kulmala, Kirkkonummi (FI); Kari Loikas, Raisio (FI); Matti Pusa, Espoo (FI)

(73) Assignee: LABMASTER OY, Turku (FI)

( * ) Notice: Subject to any disclaimer, the term of this patent is extended or adjusted under 35 U.S.C. 154(b) by 114 days.

This patent is subject to a terminal disclaimer.

(21) Appl. No.: 13/703,520

(22) PCT Filed: Jun. 10, 2011

(86) PCT No.: PCT/FI2011/000033
§ 371 (c)(1),
(2), (4) Date: Feb. 21, 2013

(87) PCT Pub. No.: WO2011/154591
PCT Pub. Date: Dec. 15, 2011

(65) Prior Publication Data
US 2013/0210166 A1      Aug. 15, 2013

(30) Foreign Application Priority Data

Jun. 11, 2010   (FI) .................................. 20100246
Jun. 11, 2010   (FI) .................................. 20100260
(Continued)

(51) Int. Cl.
*G01N 21/66*      (2006.01)
*G01N 27/327*    (2006.01)

(52) U.S. Cl.
CPC .......... *G01N 27/3276* (2013.01); *G01N 21/66* (2013.01); *G01N 27/327* (2013.01)

(58) Field of Classification Search
CPC .. G01N 27/00; G01N 27/327; G01N 27/3275; G01N 27/403; G01N 33/0031; G01N 21/26; G01N 21/76; G01N 2021/66; C12M 1/34; C12M 1/3461
See application file for complete search history.

(56) References Cited

U.S. PATENT DOCUMENTS 5,425,869 A  *  6/1995  Noding et al. ................ 204/418
6,140,045 A     10/2000  Wohlstadter et al.
(Continued)

FOREIGN PATENT DOCUMENTS

JP    2009210316 A    9/2009
JP    2009204375 A    10/2009

OTHER PUBLICATIONS

PCT/FI2011/000033—International Search Report; Oct. 4, 2011 (6 pgs).

*Primary Examiner* — Rebecca Martinez
(74) *Attorney, Agent, or Firm* — Berggren Inc.

(57) ABSTRACT

The invention relates to electrode chip (EChip) cartridge devices which are used in hot electron-induced electrochemiluminescence (HECL) and electroluminescence (EL) methods and instrumentation based on the electrical excitation of label molecules with subsequent measurement of the luminescence in order to quantitate analyte concentrations in bioaffinity assays, especially outside of central laboratories, but also in rapid screening tests.

10 Claims, 7 Drawing Sheets

(30) Foreign Application Priority Data

Jun. 15, 2010 (FI) .................................... 20100251
Jun. 16, 2010 (FI) .................................... 20100253

(56) References Cited

U.S. PATENT DOCUMENTS

| | | |
|---|---|---|
| 6,251,690 B1 | 6/2001 | Kulmala |
| 7,005,108 B2 | 2/2006 | Ala-Kleme et al. |
| 2003/0192780 A1* | 10/2003 | Ala-Kleme et al. .......... 204/291 |
| 2004/0189311 A1 | 9/2004 | Glezer et al. |
| 2006/0096866 A1* | 5/2006 | Ala-Kleme et al. .......... 205/131 |
| 2009/0178924 A1 | 7/2009 | Ala-Kleme et al. |

* cited by examiner

LOW-COST ELECTRODE CHIP VARIANTS AND METHODS FOR MULTI ANALYTE ANALYSIS AND REFERENCING BASED ON CATHODIC ELECTROLUMINESCENCE

PRIORITY

This application is national entry of PCT/FI2011/0000033 filed on Jun. 10 2011 which claims priority of FI201000260 filed on Jun. 11 2011, FI20100246 filed on Jun. 11 2010, FI20100251 filed on Jun. 15 201 and FI20100253 filed on Jun. 16 2012, all of which are fully incorporated herein by reference.

FIELD OF INVENTION

The present invention relates to analytical methods and devices exploiting the phenomenon of electroluminescence. The invention is especially suitable for point-of-need type of analysis, such as point-of-care analysis and, on the other hand, for rapid screening tests.

BACKGROUND OF INVENTION

Presently, there is a general burden need for fast, sensitive and quantitative diagnostic technologies. Such ones are suitable for wide market areas including public health, research, farming, environmental care, veterinary medicine, and certain industrial production areas. Improved sensitivity, speed, robustness, stability, and decreased cost per analysis are factors, which after being accomplished in diagnostic technologies, can find applications in quite new areas.

Very high sensitivity can be obtained with certain diagnostics instruments, but they are too expensive. On the other hand, certain methods can be inexpensive enough, exemplified by immunochromatography, but they are not applicable to certain needs of the market. Any technology, wherein a set of such demands are met, will have an important place in the future diagnostics and a huge market potential.

There is a number of different analytical principles in practical use in diagnostics: for example, assays based on radioactivity, enzyme-linked immunosorbent assay (ELISA), colorimetric assays, and assays based on fluorescence, and chemiluminescence including electroluminescence (EL). Here, EL is considered to be equivalent to any luminescence that is electrically induced. Thus, electroluminescence is considered to include both anodic as well as hot electron-induced (cathodic) electrochemiluminescence (ECL). The hot electron-induced ECL (HECL) is described in detail in U.S. Pat. No. 6,251,690, Kulmala S., et al. Each of these techniques has their role as regards to the integral of sensitivity, robustness, stability, speed, and price. The differences between the techniques reflect the function of physical limitations or advantages of the methods. For example, a drawback of the application based on radioactive compound is the decay of the label within a period of time and the extra cost of radioactive waste from both the safety and environmental viewpoint. The application of the most sensitive assays on diagnostics is limited by the complicated nature of the tests and instruments, and only experts can perform the assays. The complexity of the assay is generally directly proportional to the price of the instrument and/or the test. In the context of complex instruments, it could be mentioned the anodic electrochemiluminescence techniques are now becoming more and more popular: the instrument is a complicated laboratory robot, the handling of which needs expertise and where the measuring process involves repeated washes and preparative steps. They are factors that increase the cost of the analyses as well as increase the amount of waste and therefore will make this method impossible for the needs of small laboratories, doctors offices etc. (bedside or point of care analytics).

Commercially beneficial methods are based on the principle that the substances to be analyzed are identified and measured in mixtures by so-called label substances. In the measurements based on unique properties of biological molecules, as in immunochemical assays, the analyte to be measured (X) can be selectively sorbed from a mixture of molecules to solid-phase bound antibodies and then the bound molecules are measured with another labeled antibody selectively binding to (X). The label substances can be radioactive isotopes, enzymes, light absorbing, fluorescent or phosphorescent molecules, certain metal chelates etc., which are linked covalently to the antibody. Alternatively, the purified (X) can be marked and the amount of unknown unlabeled sample (X) can be measured by a competition reaction. The assays for DNA and RNA can be also based on the selective binding (bioaffinity). Also many other chemical and biochemical analyses can be carried out by the same principles. In order to decrease the cost and/or increase the measuring accuracy, there is presently a tendency to measure several different parameters at the same time in the sample. One possibility is to use labels showing fluorescence or phosphorescence at different wavelength or possessing different luminescence lifetimes. Different measuring principles and strategies, which can be used in immunodiagnostics, have been described in the book The Immunoassay Handbook, Edited by David Wild, Stockton Press Ltd., New York, 1994, on pages 1-618.

It is known in the prior art that organic substances and metal chelates are beneficial as label substances and that they can be excited by light or in some cases electrochemically to produce luminescence specific to the label. These methods are particularly sensitive and are well suitable for many type of bioaffinity assays. However, because the measured concentrations are extremely low, there are also case-dependent difficulties; the use of fluorescence can be disturbed, among other things, by Tyndall, Rayleigh and Raman scattering. When measuring biological substances, there is, almost without exception, after the excitation pulse, a fast-discharging high background fluorescence. Phosphorescence in the solution phase can be utilized mostly only with chelates between lanthanide ions and specially synthesized organic molecules. The drawback of the excitation techniques with the photoluminescent labels is the complexity of the instruments and the high price of the sensitive optical components.

In general, the advantage of ECL is the low price of the electrical excitation components and simpler optics. Compared to photoluminescence, several drawbacks can be avoided. Traditional anodic electrochemiluminescence with inert metal electrodes can be carried out with organic luminophores by a relative simple instrument in non-aqueous solvents. However, in bioaffinity assays, where the biggest commercial expectations are concentrated to, water solutions are applied. Biological samples are taken nearly always in non-organic solutions and therefore the measuring system should work in aqueous or at least in micellar water solutions. Only a very limited number of transition metal chelates work as ECL-labels in anodic ECL in water or micellar solutions.

Thus far, the commercially most important analytical chemical application of the anodic ECL is the method using derivatives of $Ru(bpy)_3^{2+}$-chelate, where the detection of the label occurs in micellar phase. As known from textbooks, micellar mixtures are always prone to different disturbing effects due to the uncontrolled complexity of the micellar equilibria. Similar systems can be used also in very small detection cells in capillary electrophoresis systems (A. Aurora et al., Anal. Comm. 34 (1997) 303-395.). HECL which does not depend on micelles has many crucial advantages over the anodic ECL. It can be applied both to immuno- and DNA hybridization methods (see, Blackburn, G., et al., 1991, Clin. Chem. 37: 1534-1539; Kenten, J., et al. 1992, Clin. Chem. 33: 873-879). The immunoassays and DNA or RNA probe applications by Roche Diagnostics Ltd. exploit magnetic particles by which the label substance is brought onto golden working electrode (Massey; Richard J., et al. U.S. Pat. No. 5,746,974; Leland; Jonathan K., et al. U.S. Pat. No. 5,705,402). The reproducible handling of magnetic latex particles is however in many ways difficult, therefore this method is useful only in expensive laboratory robots (e.g. Elecsys 1010 and 2010) having a complicated and precise liquid o handling system. In addition, the permanent massive golden work electrode needs long cleaning and pretreatment between each analysis (Elecsys Service Manual, p. 70).

Although in many respects superb, a drawback in the HECL in bioaffinity assays is the need of long incubation time in order to get the reacting molecules into equilibrium, which is necessary to optimize the analytical accuracy. Later, it was found out that a significant improvement in performance could be acquired by placing a thin porous film on the work electrode, and by producing CIPF-devices (US2009178924 (A1), Ala-Kleme et al.).

In conventional electrochemistry, electrodes are some times integrated on the same plane, but theoretically, this should not work while using hot electron electrochemistry, since the HECL should be emitted only in the outer edges of the working electrode (cathode) closest to the counter electrode. However, while testing we found out that, for some reasons in the electrolytic cell having sufficiently high volume of electrolyte solution the HECL is emitted evenly over the whole working electrode surface even if the counter electrodes are situated in the same plane on an electrode chip (integrated electrode chips, IEChip) normally made of insulating materials such as glass, ceramics or organic polymers.

Labmaster Ltd (Turku, Finland) has worked with their diagnostics strip for almost ten years and the solution developed by them is a rather simple device containing a single piece of oxide-coated silicon embedded in plastics and an essential multipurpose membrane to input samples and reagents for the bioaffinity assays (US2009178924, Ala-Kleme et al.). The major drawback of these strips is that all the measurements are carried out in an instrument's cell which has to be very carefully washed and cleaned between each measurement to avoid carry-over and the deterioration of the counter electrode built in the instrument is also problematic.

Recently, means to construct truly disposable cartridges with extremely accurate and reproducible electrodes which naturally also provide highly accurate results in practical analysis have been disclosed by us (FI 20100246, S. Kulmala et al., FI 20100251, S. Kulmala et al. and FI 20100253, S. Kulmala et al.). The basis of these inventions is either the use of Integrated Electrode Chips (IEChips) containing an anode and a cathode integrated on the same plane for the use in HECL detection, or Electrode/Electrode—chips (EE-Chips) including an electrode pair for any polarity made of carbon paste and usable in evoking EL of lanthanide chelate labels. The IEChips and EEChips are mainly used in disposable bioaffinity cartridges such as in cartridges for immunoanalysis or DNA-probing. IEChips and EEChips are called from now on with a combined name, electrode chip, EChip.

Quite early, we could see that, if an optically transparent working electrode and also an optically transparent counter electrode is used in HECL (M. Flakansson et al., Anal. Chim. Acta 541 (2005) 137-141.), two analytes can be determined. However, it is too expensive to include two photon counting detectors on a single instrument and a much better solution, if an electrolytical cell is invented which allows the use of only a single light detection unit. The problem of the recent inventions is that only one analyte (FI 20100246, S. Kulmala et al., FI 20100251, S. Kulmala et al.) or two analytes (FI 20100253, S. Kulmala et al.) can be determined when a single light detector is used. The present invention discloses how novel multipurpose EChips can be fabricated and used in analysis, either in multi analyte determinations, or in single analyte determinations using internal standards or standard additions or other types of referencing methods (FI 20100248, S. Kulmala et al). The priority is claimed on the basis of the applications FI 20100248, S. Kulmala et al.; FI 20100246, S. Kulmala et al.; FI 20100251, S. Kulmala et al. or FI 20100253, S. Kulmala et al. in the event that any of those is considered to prevent the novelty of the present invention.

According to the present invention, the EChips for multipurpose use can be constructed, and also a significant improvement in the use of CIPF-devices (US2009178924 (A1), Ala-Kleme et al.) is achieved utilizing disposable HECL and EL cartridges containing the above-mentioned EChips as described in the claims 1-10.

BRIEF DESCRIPTION OF DRAWINGS

FIG. 1(a) EChip composed of a circular insulating support material and electrodes fabricated onto it. (1) Circular substrate; (2) Counter electrode; (3) Working electrodes; (4) Hydrofobic are or adhesive tape confining the cell are (5). (b) An EChip diced to a rectangular shape from a larger disc or plate, same numbering as above. (c) An EChip wherein the contact pads are collected to a single edge, same numbering as above (sometimes it is useful have a rather long EChip which requires considerably longer conductor films to the electronic contact pads of the measuring instrument than shown in the FIG. 1(c).) (d) An EChip with concave mirror shape for the electrode areas. (e) An EChip with concave mirror shape with pointed electrodes having their electronic contacts through the chip (the electronic contact network on the lower surface of the chip). (f) EChip with plurality of electrodes contacted through the chip and the lid serves as a lens collecting the light and directing it to the center of the photosensitive area of the detector. (1) Substrate, (2) Working electrodes through the chip, (3) Counter electrode in the middle of the chip, (4) PDMS lid having the shape of a lens, (5) Light detector such as an avalanche photodiode or a photo multiplier tube.

DETAILED DESCRIPTION OF THE INVENTION

According to the present invention, different analyses can be performed with simple and inexpensive devices equally well as with more complicated devices, whenever the actual immunoassay or DNA hybridization is carried out either directly, or with the aid of a porous film, on the surface of EChips. Thus, a considerable improvement to earlier devices can be achieved and several analytes can be determined in a single assay, or alternatively, internal standards or especially standard additions can be applied. Still the measuring instrument and the measuring cartridge are sufficiently low-cost for point-need analysis and can be manufactured to be fully disposable. Thus, no carry-over between analyses can occur and the manufacturing of disposable assay cartridges will become much easier when no separate working electrodes and counter electrodes need not to be introduced in the cartridge, as earlier was the case.

In the current invention, we have several alternative fabrication designs. First, all the electrodes can be fabricated e.g. by vacuum evaporation or sputtering in a single step using a mask on a large insulating substrate such as plastic, glass, ceramics, etc., and finally the electrode chosen as the anode, is coated with carbon paste e.g. by screen printing or ink jetting and finally the substrate is diced into chips. Alternatively, e.g. two step or three step vacuum evaporation or sputtering can be carried out. For some substrates it is a good convention to fabricate first an initial layer of chromium as an adhesive layer and then the actual working electrode or counter electrode material is added on the chromium. In some purposes the chromium can be directly applied as a counter electrode. In those cases, it is most convenient that in the vacuum chamber there is the possibility to add another mask without the need of letting the normal atmospheric pressure to the vacuum chamber but, if the time used of deposition is not so important, the second mask masking the counter electrode areas (but not masking the working electrode areas) is added manually and aluminum or highly doped silicon is added on the areas of the working electrodes. Thus, finally we have working electrode films made of silicon or aluminum and counter electrodes made of chromium. If chromium is not considered sufficiently good counter electrode material, the chromium can be coated with a thin film of carbon paste. Alternatively, a third fabrication step is used wherein the masks are replaced by a third mask leaving only the counter electrode areas open and a thin film of platinum is added. In this case we finally have aluminum or silicon working electrodes and a platinum counter electrode/electrodes.

The use of aluminum electrodes is most convenient since it is sufficient to let them to be oxidized in an oxygen atmosphere or even in the ambient air and the EChip is ready to be coated with hydrophobic material to provide hydrofobically confined cell areas for coating with biomaterials or directly attaching in a cartridge made of e.g. plastics/polymers.

In the case of silicon working electrodes, their surfaces must be first oxidized either with a short plasma oxidation or chemical oxidation or, more inconveniently, by anodic oxidation using the fabricated final anode as a cathode during the anodization of silicon. Alternatively, silicon is anodically oxidized in situ during the HECL measurement with anodic pulses.

Sometimes the best solution after making a chromium film on the substrate is to let also aluminum or highly doped silicon to be coated onto all of the intended electrode areas and finally a layer of carbon paste is added by ink jetting or screen printing onto the intended counter electrode areas (anode areas). A good option, when carbon paste ink is wished to be the final layer on all electrodes is either to use only aluminum or only chromium as the first highly conductive layer below carbon paste layer. The aluminum/carbon paste electrodes are beneficial in the case carbon paste is leaking current through holes or voids, aluminum itself can nicely serve as a working electrode. Chromium, however, is not capable of producing HECL or EL of lanthanide chelates even if it is having an oxidized surface and its oxide film is sufficiently thin.

Depending on the fabrication scheme, the substrate is diced into chips at the appropriate stage. Normally dicing occurs immediately after the final electrode layer has been added onto the substrate disc, made of an insulating material, typically plastics or glass. However, sometimes it is better to add the biomaterials on to the working electrodes e.g. by ink jetting principles or printing principles prior to slicing.

The diced chips are added to the final cartridges after biocoating the working electrode area, or the chip itself may be directly form half of the final cartridge, normally the bottom part, and another half containing the fluidics, chambers, inlets and outlets, is added on top of the chip. This can be quite conveniently fabricated from e.g. PDMS.

Especially, when a high number of working electrodes are fabricated in the same plane (e.g. in the case of screening tests) it is preferable that the upper part of the cartridge is made to the shape of a lens, or alternatively contains an optically transparent window that has a shape of a lens, that collects the light from all the separate working electrodes to the light detector. This is beneficial also in case of low number of working electrode spots or stripes because the smaller the light sensitive area of the detector (e.g., cathode area in photo multiplier tube) is, the smaller is the noise level of the detector. Thus, this type of lens allows using cheaper or less noisy light detector devices. PDMS is an excellent material choice of this type of low-cost lens in disposable cartridges but, of course, many other optically transparent polymer materials such as polystyrene polyetehenetherephtalate, etc. are also equally well usable.

When photoluminescence is applied in screening tests with plurality of test spots it is very expensive to build a light source and detector system that can sufficiently accurately scan all the spots. In this respect our EChips based on HECL and EL with multiple working electrode spots or stripes are orders of magnitude of lower cost. In addition, in photoluminescence applications, the cartridge plastics must be chosen to be optically transparent in the UV range if the excitation light must be passed through the cartridge materials. Within our invention, it is fully sufficient that the cartridge window or lid is sufficiently optically transparent in the emission wavelength.

An alternative solution for efficient light collection is that the EChip substrate is originally made in the shape of concave mirror, which also results in the collection of light to the detector with small light sensitive area, situated in the focus of the "concave mirror" as described in one of the Examples.

Another route of making EChips is based on the use of strongly doped silicon chips as a substrate material (i) on to which working electrode areas with ca. 4-nm oxide films are fabricated and (ii) the other parts of the chip are first coated with a thick field-insulating silica layer on top of which (iii) the counter electrodes are fabricated by sputtering, vacuum evaporation or by printing with silver ink or carbon paste ink or their combined layers. In this case there is a single electronic contact to all working electrodes but separate contacts to each counter electrode. The drawback is the actual cell design in use must prevent current from flowing to the wrong working electrode area. This normally needs the use of an optically transparent lid, which separates each working electrode chamber from the others. The use of a silicon substrate is excellent in cases of screening tests, if high accuracy and reproducibility is required, and the working electrode spots are biocoated by ink jetting or printing type of coating methods.

In screening tests, a nice alternative is to fabricate the singly addressed HECL wells by (i) first making a thick thermal field oxide upon strongly doped silicon, (ii) followed by etching of the working electrode cavities and fabrication an ultra thin 4-nm thermal oxide in the bottom of the wells, (iii) adding separate platinum or other conductor electrodes on top of the field oxide (counter electrodes), (iv) adding SU-8 layer on top of the whole wafer and etching the SU-8 away from the sample cavities (sufficiently larger than the working electrode cavity so that all the working electrode counter electrode-pairs are uncovered and SU-8 finally forms separate wells which can be used in electrical excitation simply by selecting the right counter electrode.

Equally, well one can start (i) by first making an aluminum film on a plastic or glass substrate, or by gluing aluminum foil on the substrate. Then, (ii) working electrode areas are formed by printing an insulating polymer, lacquer or paint film leaving the intended working electrode areas bare or by adding an adhesive tape with the holes in the places of intended working electrode areas. After this, (iii) counter electrodes are printed on the insulating sub-layer described in the second step. Finally, (iv) the sample cavities are formed by printing another insulating film (but thicker than earlier) to form the final sample cavities with separately addressable working electrode-counter electrode pairs; this can be carried out also by a thick adhesive tape strip with right size of cavity holes in the right positions, which however, is normally not a competitive method in large scale production but is sufficient for preliminary tests.

Third fabrication line is very simple, all the electrode areas are fabricated in a single step by printing or ink jetting with carbon paste which has a sufficient conductivity. If carbon paste has a limited conductivity, this problem can be solved by printing first e.g. silver ink layer or other highly conductive layer such as conductive polymer layer and then a carbon paste layer on top of the cured highly conductive ink.

Next, the invention will be clarified further by diagrams and non-limiting examples and figures linked to them.

EXAMPLE 1

Fabrication of EChip Devices and Heterogeneous TSH Immunoassay Using EChips

Figure 1:
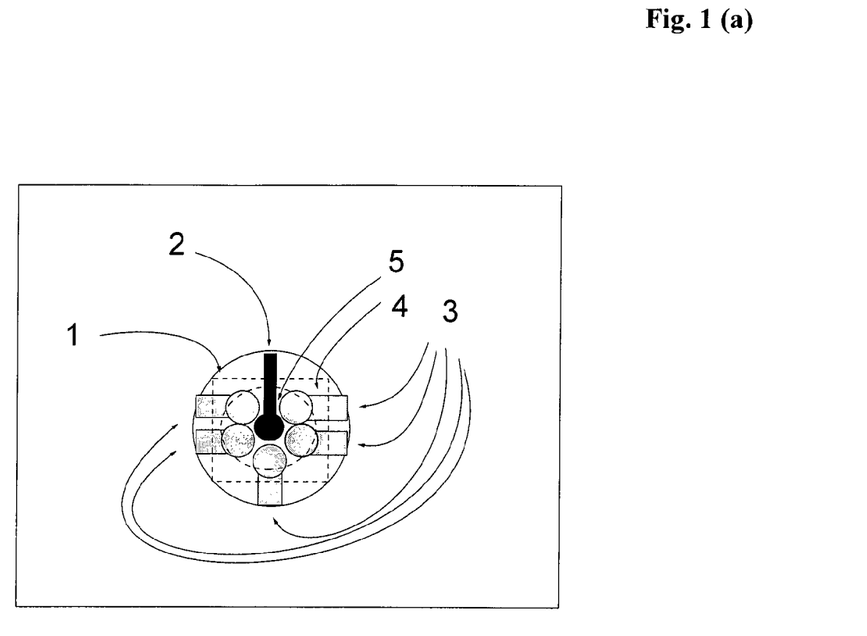

FIG. 1 displays some of our EChip variant types. Sometimes it is better to use circular plastic substrates (FIG. 1a), which quite conveniently also allow dividing the cell area to e.g. narrow sectors with the electronic contacts in the edges of the circular chip. However normally, the chips are fabricated on a large substrate plate or disc and it is most convenient to dice the chips in the rectangular shape. The smaller the working electrodes are, the more preferable it is to add biocoatings such as antibodies, antigens, oligonucleotides etc. by using ink jet type of dispensing. In the actual test we chose to use specimens, which had considerably large working electrode spots.

When very small electrode spots (screening tests) are used on a relatively large cell area it is sometimes preferable to use substrates that have been made to a shape of a concave mirror by molding, hot embossing, etc. and the light detector is placed in the focus of this imaginary mirror (FIG. 1d). A good option in these kind of devices was found to be conductor rods embedded in PDMS with the conductor rod ends coated with carbon paste. This type of device was tested by embedding a bunch of aluminum wires (30 wires around one a bit larger stainless steel rod) (anode) in PDMS in a mold (diameter 20 mm). The inner surface of the "concave mirror" was then mechanically polished to be sure that all the electrodes were uncovered from PDMS with very smooth sanding paper and finally with aluminum oxide slurry in water. After this electrodes were left to be oxidized in air overnight. With the test with 1 micromolar Tb(III) chelate solution each of the pointed working electrodes produced by the aluminum wires were observed to work, but the CV was 12% which indicates that the shape of the "concave mirror" was not perfect. A simple means to fabricate a plurality of pointed electrodes in PDMS and other type of polymers is to first make the holes through the chip and then fill the holes with conductive ink which is preferably sufficiently conductive carbon paste ink but can be also e.g. silver ink which is finally coated with carbon ink to provide a carbon paste electrode on the chip with silver ink contact to it. Porous ceramic materials and e.g. porous aluminum oxide filters allow the fabrication of a plurality of very small pointed HECL electrodes by melting aluminum in the pores and arranging the contacts from below which, however, is not very easy.

In the first tests with bioaffinity assays we chose to use specimens, which had considerably large working electrode spots. EChips of the type presented in FIG. 1(c) were fabricated on a glass wafer. First, the glass wafer was shortly plasma etched. After this, a layer of chromium (99.99%, Alpha Ventron) was sputtered on all the electrode areas through a mask (2 and 3 in FIG. 1(c)). Then a layer of aluminum (99.99%, Alpha Ventron) was sputtered on the chromium film through another mask that screened the counter electrode area (i.e. working electrodes (3 in FIG.

1(c). In the next step, platinum was sputtered using a third mask screening the working electrode areas (i.e. platinum counter electrodes were fabricated, 2 in FIG. 1(c)). Then the wafer was diced into 20 mm×20 mm rectangular pieces and the chips were transferred to a dessicator and the aluminum electrodes were left to be oxidized in an oxygen atmosphere overnight at room temperature.

The cell area of the EChips (5 in FIG. 1(c)) was coated using the aid of the hydrophobic ring on them, which was produced by an adhesive tape with a hole confining a cell area with diameter of 11.0 mm. The coating solution (180 µL) composed of 0.1 M MES, 0.03 M $H_3BO_3$, 0.5 mM K-citrate, 0.025% glutaraldehyde, 0.05% bovine gamma-globulin and 10 µg/mL of antibody (MIT0406 MOAB anti hTSH Medix Biotech Inc. USA). After incubation for two hours at room temperature in the closed plastic box the coating solution was aspirated and the wells were washed two times with washing solution (50 mM Tris-HCL, pH 7.8, containing 0.9% of NaCl, 0.09% $NaN_3$ and 0.05% Tween 20. The wells were then saturated by adding 180 µL of saturation solution (50 mM Trizma base, 0.1% BSA, 0.1% NaN3, 0.1% Tween 20, pH 7.5 adjusted with $H_2SO_4$). After saturation the IEChips were allowed to dry at 30° C. for 2.5 hours.

Labeled antibody (monoclonal anti-hTSH, clone 5404, 5.5 mg/mL, Medix Biochemica Oy Ab) was prepared by allowing an isothiocyanate derivative of Terbium (III) chelate (Tb-2,6-bis[N,N-bis(carboksymethy)aminomethyl]-4-bentsoylphenol chelate) to react in 80 times molar excess at pH 9.5 for over night at room temperature. A column 1 cm in diameter filled to 5.5 cm with Sephadex G-50 and for a further 52 cm with Sepharose 6B was used to separate the conjugated protein fraction from excess reagent.

The immunoassay was based on the use of porous film (thickness 6-11 um, $1 \times 10^5$-$6 \times 10^8$ holes/$cm^2$, Whatman). The labeled antibody (0.5 µL, 80 µg/mL) in 50 mM Tris-HCl buffer, pH 7.7, containing 0.05% $NaN_3$, 0.9% NaCl, 0.5% BSA, 0.05% bovine gammaglobulin and 0.01% Tween 20 was pipetted onto the 11×11 mm membrane pieces and they were allowed to dry at room temperature over night.

The standard samples (TSH concentrations 10.0, 30.0 and 100.0 mIU/L) were prepared in test tubes by diluting TSH standard solution (Wallac, DELFIA hTSH kit, 324 mIU/mL TSH) with dilution solution (50 mM Trizma base, 0.05% $NaN_3$, 0.9% NaCl, 0.5% BSA, 1 mM $CaCl_2*H_2O$, pH 7.7 adjusted with HCl).

For the immunoassay the membrane pieces containing the dried labeled secondary antibody were attached on the hydrophilic electrode area designed to form the electrolytic cell with an electrolytic solution droplet. A 10-µL of sample from 30.0-mIU/L TSH standard solution was pipetted onto the center of the porous film on the EChip. The sample dissolved the labeled antibody and filled fast the cavity between the membrane and electrode network. After 8 minutes the immunoreaction was sufficiently close to equilibrium, and the membrane was removed by using tweezers. The EChip was washed twice with combined washing/measuring solution (50 mM $Na_2B_4O_7$, 0.1% $NaN_3$, 0.003% Tween 20, pH 7.8 adjusted with $H_2SO_4$).

Then, 120 µL of measuring buffer was added and the TR-HECL (time-resolved HECL) intensity was measured with an electrochemiluminometer by switching the pulse generator in turn to each working electrode. The measuring instrument was composed of Stanford Research Instruments SR 400 gated photon counter, Nucleus MCS multiscaler card and a home made coulostatic pulse generator and a home made cell compartment (black plastic) and a Perki-nElmer photon counting CPM module. Pulse amplitude was −25 V, pulse charge 15 µC/pulse, pulse frequency 20 Hz, the TR-HECL intensity was integrated over 100 excitation cycles, delay time 0.05 ms and gate time 6.0 ms.

Thus 5 replicate measurements from the same sample were rapidly obtained. The signals were: 875, 814, 856, 802 and 819 photon counts. Thus, the mean was 832.2 and CV 3.7%. In this way, a calibration curve with 5 replicate measurements on each concentration can be measured fast.

When placings of pointed working electrodes according to FIG. 1(e) and FIG. 1(f) were tested with Tb(III) chelate solution, it was observed that only a minor improvement could be obtained with concave electrode support in comparison to planar electrode support. However, somewhat better results were obtained with the relatively large PDMS lens setup presented in FIG. 1(f).

EXAMPLE 2

Standard Addition Method Using

The EChips were fabricated as in Example 1, but instead of attaching an adhesive tape with a single large circular hole in it, a Teflon sticker (Irpola Oy, Turku, Finland) of thickness of 0.25 mm with five round holes exactly matching the size of the working electrodes (diameter 3.0 mm) was attached on the electrode chip.

The working electrode areas of EChips were coated by adding the coating solution (50 µL) composed of 0.1 M MES, 0.03 M $H_3BO_3$, 0.5 mM K-citrate, 0.025% glutaraldehyde, 0.05% bovine gamma-globulin and 10 µg/mL of antibody (MIT0406 MOAB anti hTSH Medix Biotech Inc. USA). After incubation for one hour at room temperature in the closed plastic box the coating solution was aspirated and the adhesive tape wells were washed two times with washing solution (50 mM Tris-HCL, pH 7.8, containing 0.9% of NaCl, 0.09% $NaN_3$ and 0.05% Tween 20). The wells were then saturated by adding 50 µL of saturation solution (50 mM Trizma base, 0.1% BSA, 0.1% $NaN_3$, 0.1% Tween 20, pH 7.5 adjusted with $H_2SO_4$). After saturation the EChips were allowed to dry at 30° C. for 2.5 hours.

A sample was taken from 30.0-mIU/L hTSH standard solution and it was divided in five 30-µL aliquots in test tubes. To two of them only 10.0 µL of assay buffer was added and mixed, to the next 30-µL aliquot 3.0 µL of 324-mIU/mL hTSH standard and 7.0 µL of assay buffer was added and mixed, then 6.0 µL of 324-mIU/mL hTSH standard and 4.0 µL of assay buffer was added in the next aliquot and mixed, and finally 9.0 µL of 324-mIU/mL hTSH standard and 1.0 µL of assay buffer was added and mixed. Then 25-µL samples from each test tubes were pipetted together with 1.0 µL of labeled antibody (40 µg/mL in 50 mM Tris-HCl buffer, pH 7.7, containing 0.05% $NaN_3$, 0.9% NaCl, 0.5% BSA, 0.05% bovine gamma globulin and 0.01% Tween 20) into the miniature adhesive tape wells. After 15 minutes incubation the chip was washed with running wash solution (50 mM Tris-HCL, pH 7.8, containing 0.09% $NaN_3$ and 0.05% Tween 20) and the tape was removed and replaced by a PDMS slide (with a thickness of 2.0 mm and a circular hole through the PDMS chip providing the final measuring cell) which was clamped onto the EChip and 200 ml of measuring buffer was added (50 mM $Na_2B_4O_7$, 0.1% $NaN_3$, 0.003% Tween 20, pH 7.8 adjusted with $H_2SO_4$).

Figure 2:
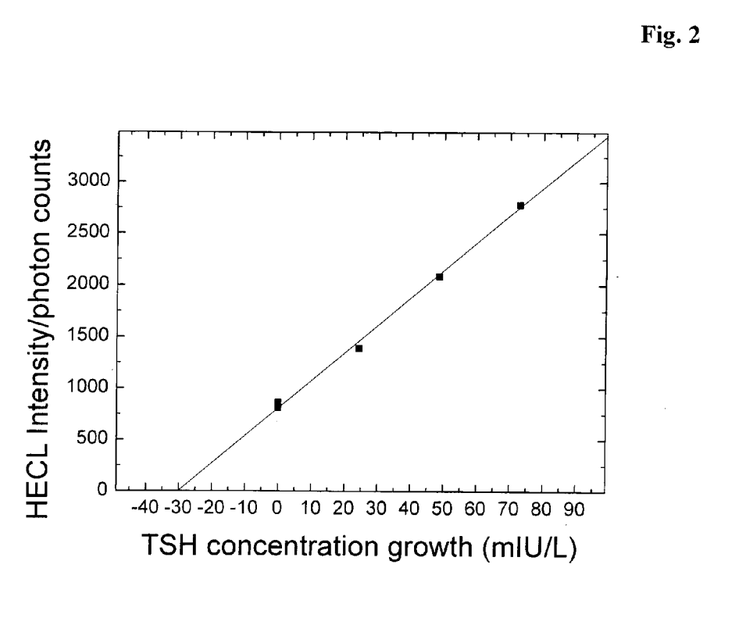
FIG. 2. Standard addition method in hTSH assay on an EChip.

Finally, the HECL intensity from each working electrode was measured in turns using the same measuring parameters as in Example 1. The results are presented in FIG. 2.

EXAMPLE 3

Simultaneous Determination of TSH and CRP on an EChip

C-reactive protein (hCRP) and thyroid stimulating hormone (hTSH) were determined simultaneously. One of the working electrodes was coated with both of the catching antibodies, two of the working electrodes were coated with hTSH-catching antibody and the rest two with hCRP-catching antibody. Anti-hTSH and anti-hCRP were labeled with an isothiocyanate derivative of Terbium (III) chelate (Tb (III)-2,6-bis[N,N-bis(carboksymethyl)aminomethyl]-4-bentsoylphenol chelate) analogously to Example 1.

EChips of the type presented in FIG. 1(c) with silicon electrodes were fabricated on a glass wafer by sputtering and using n-type silicon wafers as a source of doped silicon (0.005-0.018 Ω·cm resistivity and (111) orientation, Okmetic Oy, Finland). The electrodes were left to be oxidized in an oxygen atmosphere overnight at room temperature in a desiccator. The counter electrode was then layered by carbon paste (Creative Materials 110-04 Carbon Ink, Tyngsboro, Mass., USA) manually through a mask on the chips and the carbon paste was left to be cured overnight.

The coating with primary antibodies was carried out using Teflon stickers producing micro wells for incubation steps as in example 2. 30 μL of Anti-hTSH (125 μg in 30 μl, anti-hTSH, MIT0406, Medix Biotech Inc. USA, 0.1 M MES, 0.03 M borate, 0.5 mM K-citrate, 0.025% glutaraldehyde, 0.05% bovine gamma globulin) was pipetted on each micro well chosen and incubated 2 hours at room temperature together with anti-CRP coating (below). Three of the micro wells were coated with anti-hTSH as mentioned above and two with anti-hCRP. 30 μL of anti-hCRP (anti-hCRP, 6404, Medix Biochemica Oy, Finland, 100 μg in 30 μl, 50 mM Tris-HCl-buffer, pH 7.8, 0.05% $NaN_3$, 0.9% NaCl, 0.05% bovine gamma globulin) was pipetted in the micro wells still left. Incubation time was 2 hours as mentioned above.

The micro wells were then washed twice with the wash solution (50 mM Tris-HCl buffer, pH 7.8, 0.9% of NaCl, 0.09% $NaN_3$, 0.05% Tween 20) and aspirated empty. Then the electrodes were saturated by pipetting 30 μL of saturation solution (50 mM Tris-HCl, pH 7.8, 0.05% $NaN_3$, 0.9% NaCl, 0.1% BSA, 6% D-sorbitol) and incubated for 45 minutes. Then the micro wells were aspirated empty and let to be dried in 30° C. for 2.5 h.

For the dual immunoassay following standard solutions were made: hCRP 0 ng/ml and hTSH 0 mIU/ml (blank solution); hTSH 10 mIU/ml; hTSH 100 mIU/ml, hCRP 10 ng/ml, hCRP 100.

In the immunoassay step, 20 μl of standard solutions of hTSH was added to the wells 2-3 and 1.0 μl of the labeled anti-hTSH (80 μg/ml, clone 5404, Medix Biochemica Oy Ab, 50 mM Tris-HCl buffer, pH 7.7, 0.05% $NaN_3$, 0.9% NaCl, 0.5% BSA, 0.05% bovine gamma globulin, 0.01% Tween 20, 1 mM $CaCl_2$*$H_2O$) was added.

Also, 20 μl of standard solutions of hCRP were added to the wells 4-5 and 1.0 μTb chelate-labeled anti-hCRP solution (74 μg/ml, Medix Biochemica Oy Ab anti-hCRP clone 6404, pH 7.7, 0.05% NaN3, 0.9% NaCl, 0.5% BSA, 0.05% bovine gamma globulin, 0.01% Tween 20, 1 mM CaCl2*H2O). Blank solution was added in an analogous way to well 1.

Figure 3:
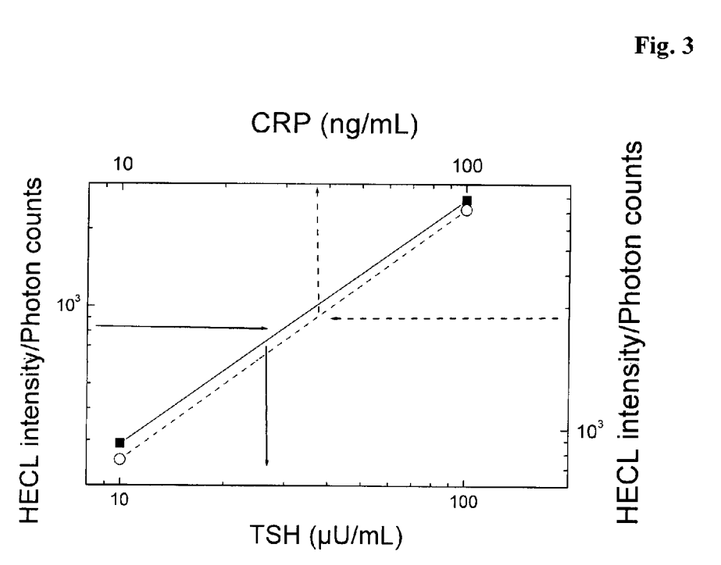
FIG. 3. Dual immunoassay on an EChip with silicon working electrodes.

After 15 minutes incubation time the wells were washed with measuring buffer (0.05 M sodium tetra borate buffer adjusted to pH 7.8 with sulphuric acid, 0.1% $NaN_3$) and the original Teflon sticker was carefully removed and replaced by an adhesive tape leaving a circular cell in use with the diameter of 11.0 mm. 120 μl measuring buffer was added and the HECL intensities were measured in turns for each of the electrodes using the same measuring parameters as in Example 1 except that just before the measurements 20 anodic 6 V pulses (20 μC/pulse) were given to the working electrodes. The results are presented in FIG. 3. When the EChips of Example 1 were tested, somewhat better results were obtained than with the silicon electrodes of the present example.

EXAMPLE 4

Simultaneous Determination of TSH and CRP on a EChip with Carbon Paste Electrodes We have recently noticed that Tb(III) labels can be excited at carbon paste electrodes (FI 20100253, S. Kulmala et al.) and the measurements presented below confirm that this EL with unknown mechanism is clearly of cathodic origin. The power of these electrodes and this EL is that the electrodes can be nicely used both as cathodes or anodes and thus even both polarities can be used during a single measurement when there is some reason for this.

The chip for this experiment was originally fabricated for Example 1. The electrodes already present on the chip were coated with carbon paste (Creative Materials 110-04 Carbon Ink, Tyngsboro, Mass., USA) through a mask emulating screen-printing. The carbon paste was left to be cured at room temperature for 24 h.

Figure 4:
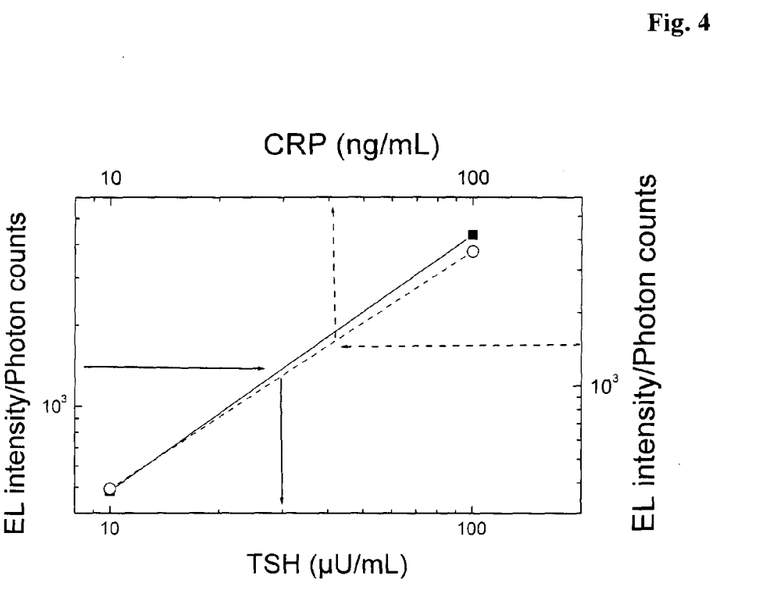
FIG. 4. Dual immunoassay on an EChip with silicon working electrodes.

The dual immunoassays of hTSH and hCRP were then carried out as in Example 3, except that the measuring buffer was 0.05 M $Na_2B_4O_7$ (pH 9.2, containing $2 \times 10^{-4}$ M $K_2S_2O_8$) and the pulse voltage was −35 V. The results are presented in FIG. 4.

EXAMPLE 5

EChip for Screening Purposes

Figure 5:
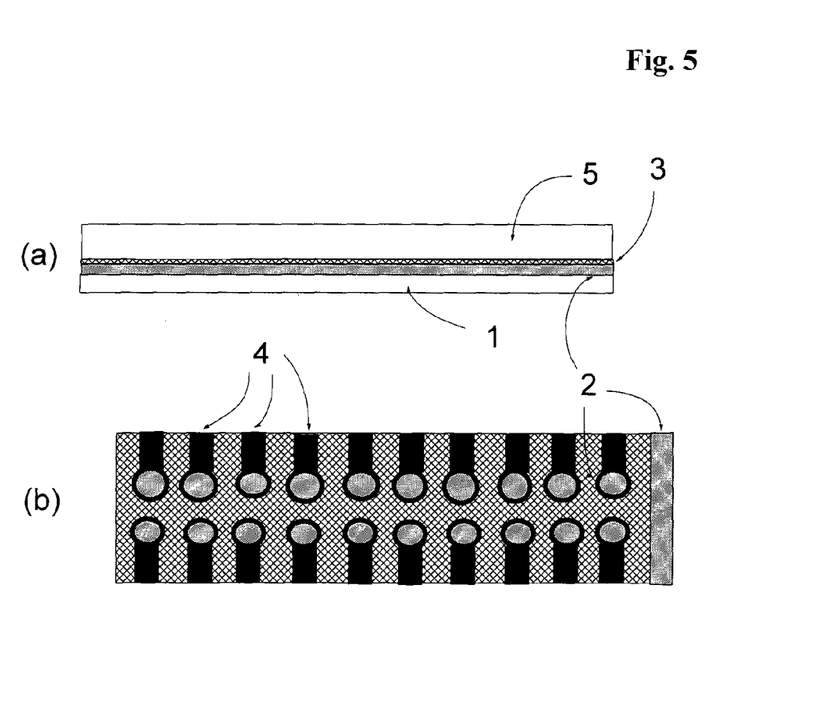
FIG. 5. 20-position EChip for screening purposes. (a) Side view. (b) From up. (1) Insulating or conducting support, (2) Vacuum-evaporated or sputtered aluminum film or aluminum foil glued on top of the support, (3) An insulating film (thicker than ca. 300 nm) created by printing or being an adhesive insulating tape with the cavity holes in appropriate places, (4) Carbon paste electrodes on top of the silver ink upon the thick insulating film around the working electrode cavities with the contact pads in the chip sides, (5) Thick polymer layer which determines the final size of the sample cavity leaving both the working electrode and the counter electrode around the working electrode bare, e.g. a second adhesive tape, printed polymer layer or PDMS chip attached on top of the EChip.

A simple EChip for screening tests was fabricated by gluing an aluminum foil (Pirkka Vahva Alumiinifolio, Kesko Oyj, Finland) on a plastic chip (10×36 mm). Silver ink (Bison electro G-22, Bison Inc, Netherlands) was painted on an adhesive film meant for covering books through a mask so that counter electrode shapes were created (4, FIG. 5). After the silver ink had been cured another layer was added with the same mask but now with carbon paste (Creative Materials 110-04 Carbon Ink, Tyngsboro, Mass., USA). After the counter electrodes had been screen-printed in this way the holes through the adhesive tape covered by the counter electrodes were carefully made with a cork drill (diameter of the holes 3.0 mm) using a mask as a positioning tool. Then the adhesive tape film was attached on the aluminum foil so that the right end of the aluminum foil was left bare for making the electronic contact to the working electrode (FIG. 5). After this, A Teflon sticker (thickness 0.25 mm, Irpola Oy, Turku, Finland) with cavity holes made with a 4-mm cork drill was attached on top of the earlier adhesive layer. Thus, sample cavities of height of 0.25 mm and diameter of 4.0 mm were created. In the bottom of the cavities there was a circular working electrode of diameter of 3.0 mm and around it was a circular carbon paste counter electrode with the width of 0.5 mm. The only problem with this chip was that, it had to be moved in the right position in the light measuring cavity of our electrochemilumineter, i.e. only two measurements could be carried out in a single position and then the chip had to be moved again in the right position. In an actual product, this can be easily be provided by a stepper motor which presently is not too expensive.

Figure 6:
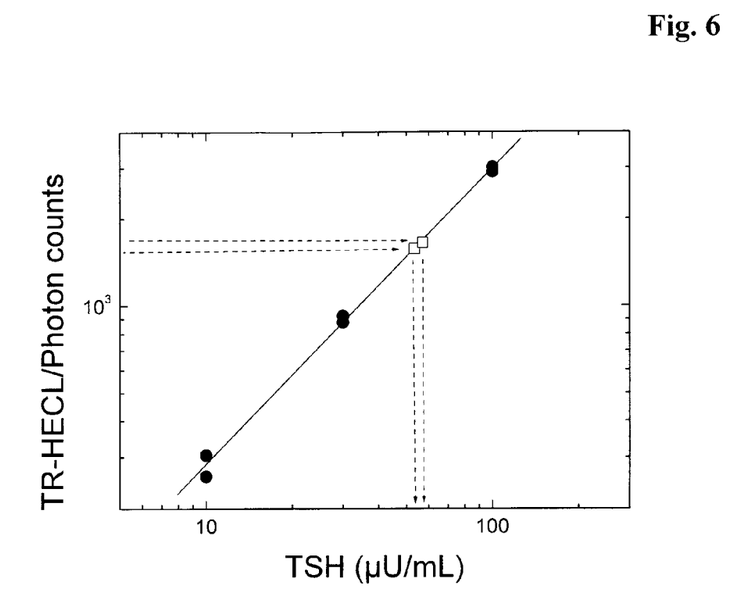
FIG. 6. An immunoassay using 20-position EChip based on aluminum foil working electrodes.

These kind of separately electrically addressable cavities can be initially biocoated with the desired material or this kind of chips can equally well be used in quantitative multianalyte determinations, in utilizing standard addition measurements or getting a large number of replicate measurement from a single analyte. In our case, we coated the sample cavities with anti-hTSH antibodies and carried out hTSH measurements as in Example 1 using the same standard solutions but now producing two separate blank determinations, calibration curve of three standards with duplicate measurements and "an unknown" sample produced by mixing of standards 10 mIU/L and 100 mIU/L with a ratio 1:1 (i.e. the concentration of the sample was 55 mIU/L, i.e. 55 μIU/mL). The calibration plot and the determinations of the sample are shown in FIG. 6.

EXAMPLE 6

EChip for Screening Purposes with Carbon Paste Electrode Pairs

First, a similar chip was constructed as in Example 5, except that the aluminum foil surface was first coated overall with the same carbon paste used in the previous Example. Thus, separately addressable carbon-carbon electrode pairs in separate cavities were created. Their functionality was tested with 1.0 micromolar solution of Tb(III)-2,6-bis[N,N-bis(carboksymethyl)aminomethyl]-4-bentsoylphenol chelate (pH 9.2, $2\times10^{-4}$ M $K_2S_2O_8$, pulse voltage −65 V, pulse charge 25 μC/pulse, pulse frequency 20 Hz, TR-EL (time-resolved electroluminescence) intensity was integrated over 1000 excitation cycles, delay time 0.05 ms and gate time 6.0 ms. The CV was observed to be 9.2% which is not bad for these hand-made devices. The electrodes easily withstood 1000 excitation cycles without loosing any of the original EL intensity.

EXAMPLE 7

Figure 7:
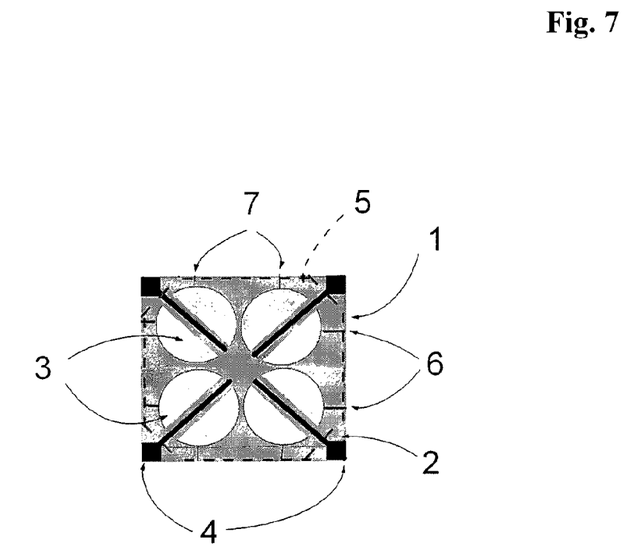
FIG. 7. Silicon-based 4-position EChip cartridge with a capillary-filling PDMS chamber. (1) Silicon chip, (2) Thick field oxide (all the gray areas), (3) Ultra thin 4-nm oxide film upon working electrode areas (all light gray areas), (4) Counter electrodes with the contact pads made on top of the field oxide (black), (5), PDMS-lid leaving the corners of the chip open for electrical contacts to the separate counter electrodes, (6) Inlet micro channels to the sample chamber (one for each sample chamber), (7) Air outlet micro channels (only one of the 3 is drawn).

Standard Addition Method Simulating HECL Energy Transfer Assays in which no Biocoating of the Electrodes is Required on Silicon-Based EChip Cartridge The chip is composed of high-conductivity silicon (1, FIG. 7), which is thermally oxidized to yield a thickness of over 300 nm for the surface oxide film (2, FIG. 7). This field oxide serves as electrical insulation between the counter electrode metallization and the silicon substrate. It is wet etched from the working electrode areas, where the 4 nm thick tunneling oxide is formed by thermal oxidation. The darker gray areas in the figure indicate where the field oxide remains.

Four wire type counter electrodes were fabricated by depositing 200 nm of platinum with a 10-nm layer of chromium underneath to promote adhesion (4, FIG. 7). This metallization was patterned by lift-off to form the counter electrodes in the sample cell areas, and contact pads at each corner of the chip The metallization is denoted by black color in the figure.

The backside of the chip is etched free of oxide and metallized with aluminum to improve electrical contact and the wafer was diced to chips (20×20 mm). A PDMS lid was created by casting the PDMS base and curing agent mixture onto a master mould. After curing, the lid was peeled off the mould and bonded onto the electrode chip to form the sample chambers (3, FIG. 7), sample inlet channels (6, FIG. 7) and air outlet channels (7, FIG. 7). The area surrounded by a dashed line in the figure denotes the PDMS lid (5, FIG. 7), which leaves the contact pads of counter electrodes bare in the corners of the chip.

Within the lid, PDMS directly contacts the electrode chip, except the areas that are channels or sample chambers. Within the round sample chambers (3, FIG. 7), rectangular pillars contacting the chip support the ceiling of the chamber. The volume of the sample chamber was 15.0 μL.

Tb(III)-2,6-bis[N,N-bis(carboksymethyl)aminomethyl]-4-bentsoylphenol chelate was a model analyte in this experiment. The "unknown" analyte concentration in the sample was 100 pM. In the test, the first sample chamber was left empty and to the other three chambers 3.0, 6.0 and 9.0 μL of 1.0 micromolar Tb(III) chelate solution were pipetted, respectively, and the lid was let to dry (i.e. 3.0 , 6.0 and 9.0 pmol of the chelate were added in the chambers). The lid was put on the EChip in a frame that secured sufficient pressure between the PDMS-lid and the EChip to make it air and watertight.

The right and left edges of the PDMS-EChip were dipped in turns in the sample solution (100 pM solution of the Tb(III) chelate) and the fluid was drawn by capillary force through the inlet channel (6, in FIG. 7) into the four sample chambers. As the chambers were filled, air escaped via the thinner channels to the edge of the PDMS lid (7, FIG. 7, only one of three air outlet channels of each chambers is drawn in the figure).

Figure 8:
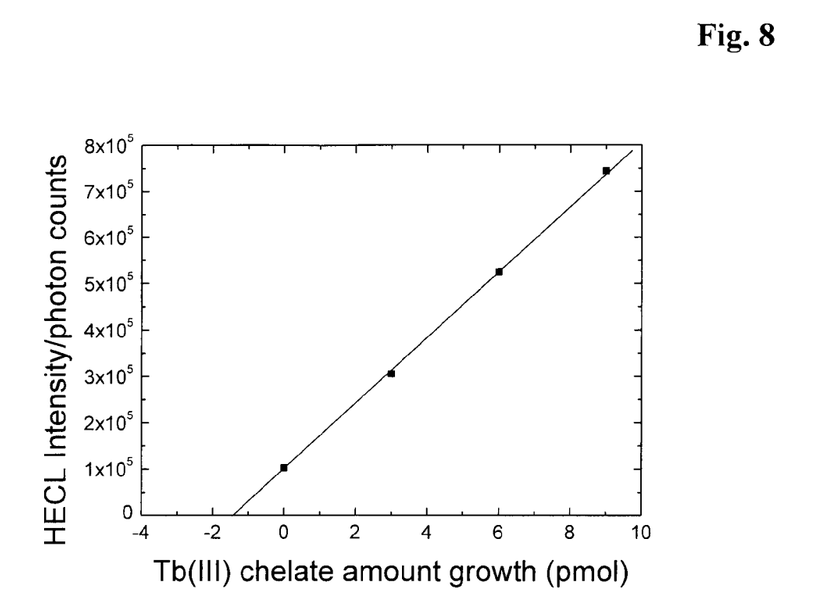
FIG. 8. Standard addition method using silicon-based 4-position EChip cartridge.

Thus, one of the chambers contained only the sample, and the others the sample+added standards. The chip was incubated for 8 minutes for dissolving the added standards and the HECL intensities were measured as in Example 2, except that now the pulse voltage was −30 V, pulse charge 20.0 μC/pulse and HECL was integrated over 1000 excitation cycles. The working electrode areas were so large in the present chip that the chip had to be repositioned in the measuring chamber for each measurement. FIG. 8 shows the standard addition plot of the experiment.

The invention claimed is:

1. A cathodic electrochemiluminescent analytical device to determine an amount of an analyte, said device comprising a disposable assay cartridge and a time resolved luminescene measurement instrument, said essay cartridge comprising an electrode chip wherein:
   one or more working electrodes and one or more counter electrodes are integrated on the chip on one plane,
   the material of the one or more working electrodes being a conductor or strongly doped semiconductor both of which are covered by an electrical insulator layer having a thickness of 0.5 to 50 nm and the working electrodes serving as cathodes of the device,
   the one ore more counter electrodes being made of metal by sputtering or vacuum evaporation or other standard metalization procedures or by printing with conductive ink or dipping in an conductive ink, and the counter electrodes serving as anodes of the device,
   the working electrodes and the counter electrodes having contact strips to an end of the electrode chip or corners of the chip, or through the chip, by which the electrodes can be connected to excitation electronics of the luminescence measurement instrument, and wherein a sample to be analyzed is capable of giving a luminescence signal proportional to the amount of the analyte during or after applying excitation pulses of 35-65 V to the chip.

2. The device according to claim 1, wherein the working electrodes are made of silicon or aluminum and their surfaces contain an oxide layer of 0.5-50 nm of thicknes and intended anode areas of the chip are fabricated by first adding an insulating film of at least 200 nm of thickness onto the intended anode areas of the chip and successively coated with a conductive film by vacuum evaporating or sputtering an additional metal film or by printing or ink jetting a conductive film upon the anode areas of the device.

3. The device according the claim 1, wherein all the electrodes are fabricated from carbon paste or from silver ink or other conducting ink which may further be coated with a carbon paste layer.

4. The device according claim 1, wherein a porous film of thickness less than 100 μm is brought onto the electrodes, said film being capable of receiving a sample to be analyzed and reagents to react with the sample, and the sample being capable to give during or after the pulses aluminescence signal which is proportional to the amount of the analyte.

5. The device according to claim 1, wherein the cartridge is a polymer cartridge having an entrance inlet and a multitude of cavities, wherein the cavities of the cartridge are capable to be filled either by capillary forces, pressure or suction, wherein when a sample or a diluted sample is filling the cavities it dissolves reagents in the entrance inlet, and the sample is capable to give luminescence signal which is proportional to the amount of the analyte.

6. The device according to claim 1, wherein the cartridge has a lid or an upper part, said lid or upper part of the cartridge having a shape of a lens, or a disposable lens is embedded in the lid or upper part of the cartridge, and said lens is suitable to collect light from the plurality of working electrodes and guiding the light to a light sensitive area of a detector of the luminescence measuring instrument.

7. A method for a bioaffinity assay carried out on the electrode chip of claim 1, wherein polarity of the working and counter electrodes is changed at least once during the excitation.

8. A method for a bioaffinity assay carried out on the integrated electrode chip of claim 1, wherein the electrode chip is either fully embedded in a polymer cartridge or just covered by a polymer lid, and wherein the cartridge or the lid provides cavities for inlet of samples and reagents and further provides a chamber for combined reaction of the sample and the reagents and hot electron-induced electrochemiluminescence for excitation of electrochemiluminescent labels used in the assay.

9. The device of claim 1, wherein the device comprises one anode and a plurality of cathodes, or one cathode and a plurality of anodes or a plurality of anodes and cathodes.

10. The device of claim 6, wherein the cavities are capable of being washed once with a measuring buffer prior to excitation.

* * * * *